United States Patent [19]

Weiler et al.

[11] 4,062,859

[45] Dec. 13, 1977

[54] HALOGENATED 3-ISOTHIAZOLIDINONE 1-OXIDE AND 1,1-DIOXIDES

[75] Inventors: Ernest D. Weiler, Ambler; George A. Miller, Glenside, both of Pa.

[73] Assignee: Rohm and Haas Company, Philadelphia, Pa.

[21] Appl. No.: 606,618

[22] Filed: Aug. 21, 1975

[51] Int. Cl.$^2$ .......................................... C07D 275/02
[52] U.S. Cl. .................................... 260/302 A; 71/67; 71/91; 260/301; 424/270
[58] Field of Search ............................ 260/302 A, 301

[56] References Cited

U.S. PATENT DOCUMENTS 3,635,997   1/1972   Toepfl ............................ 260/302 A

*Primary Examiner*—R. Gallagher
*Attorney, Agent, or Firm*—Bernard J. Burns; George W. F. Simmons; William E. Lambert, III

[57] ABSTRACT

The preparation and use of halogenated 3-isothiazolidinone 1-oxides and 1,1-dioxides are disclosed. These compounds and compositions containing them are useful in controlling weeds and microorganisms such as bacteria, fungi, algae and the like.

9 Claims, No Drawings

HALOGENATED 3-ISOTHIAZOLIDINONE 1-OXIDE AND 1,1-DIOXIDES

This invention relates to certain novel substituted 3-isothiazolidinone-1-oxides and 1,1-dioxides, to biocidal compositions containing them and to their utilization in the control of weeds and microorganisms such as bacteria, fungi, algae and the like.

The novel compounds of this invention may be represented by the formula

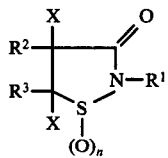

wherein $R^1$ is a hydrogen atom; an alkyl group, preferably having 1 to 18 carbon atoms; cycloalkyl group, preferably having a 3 to 8 carbon atom ring and up to 12 carbon atoms; an aralkyl group, preferably having up to 10 carbon atoms; an aryl group, preferably having up to 10 carbon atoms; $R^2$ and $R^3$ are independently a hydrogen atom, a halogen atom or an alkyl group of from 1 to 4 carbon atoms; X is a halogen atom; and $n$ is the integer 1 or 2.

The term "alkyl" as used in the specification and claims is meant to include branched and straight chain aliphatic hydrocarbons of up to 18 carbon atoms which can be unsubstituted or substituted with substituents such as hydroxy groups, halogen atoms, carbalkoxy groups, cyano groups, carboxy groups and the like.

The term "aralkyl" as used in the specification and claims is meant to include aralkyl groups of up to 10 carbon atoms preferably benzyl which can be unsubstituted or substituted with up to two substituents selected from the group consisting of halogen atoms, ($C_1$–$C_4$) alkyl groups, ($C_1$–$C_4$) alkoxy groups, nitro, cyano and the like.

The term "aryl" as used in the specification and claims is meant to include phenyl or naphthyl groups which can be unsubstituted or substituted with up to two substituents selected from the group consisting of halogen atoms, ($C_1$–$C_4$) alkyl groups, nitro group and the like.

The preferred compounds of this invention are those wherein $n$ is the integer 1 and $R^1$ is a hydrogen atom; a ($C_1$–$C_{18}$) unsubstituted alkyl group; a ($C_3$–$C_8$) cycloalkyl group; an unsubstituted benzyl group or a halogen- ($C_1$–$C_4$) alkyl- or ($C_1$–$C_4$) alkoxy- substituted benzyl group; a phenyl group or a halogen-methyl- or nitro-substituted phenyl group; a ($C_1$–$C_4$) hydroxyalkyl group; a ($C_1$–$C_4$) haloalkyl group; a ($C_1$–$C_4$) carbalkoxyalkyl group; a ($C_1$–$C_4$) cyanoalkyl group or a ($C_1$–$C_4$) carboxyalkyl group; X is a halogen atom; and $R^2$ and $R^3$ are independently hydrogen or chlorine atoms.

A more preferred embodiment of this invention are those compounds wherein $n$ is the integer 1; X is a halogen atom; $R^1$ is a hydrogen atom or a ($C_1$–$C_8$) alkyl group; and $R^2$ and $R^3$ are hydrogen atoms.

Typical compounds which are encompassed by this invention include:

4,5-dichloro-3-isothiazolidinone 1-oxide
2-ethyl-4,5-dichloro-3-isothiazolidinone 1-oxide
2-pentyl-4,5-dichloro-3-isothiazolidinone 1-oxide
2-t-octyl-4,5-dichloro-3-isothiazolidinone 1-oxide
2-octadecyl-4,5-dichloro-3-isothiazolidinone 1-oxide
2-cyclohexyl-4,5-dichloro-3-isothiazolidinone 1-oxide
2-(2-hydroxyethyl)-4,5-dibromo-3-isothiazolidinone 1-oxide
2-(2-bromomethyl)-4,5-dichloro-3-isothiazolidinone 1-oxide
2-cyanomethyl-4,5-dichloro-3-isothiazolidinone 1-oxide
2-carboxymethyl-4,5-dichloro-3-isothiazolidinone 1-oxide
2-(2-carbomethoxyethyl)-4,5-dichloro-3-isothiazolidinone 1-oxide
2-phenyl-4,5-dichloro-3-isothiazolidinone 1-oxide
2-(3,4-dichlorophenyl)-4,5-dichloro-3-isothiazolidinone 1-oxide
2-benzyl-4,5-dichloro-3-isothiazolidinone 1-oxide
2-propyl-4,5-dimethyl-4,5-dichloro-3-isothiazolidinone 1-oxide
2-hexyl-4-methyl-5-ethyl-4,5-dichloro-3-isothiazolinone 1-oxide
4,5-dichloro-3-isothiazolidinone 1,1-dioxide
2-isopropyl-4,5-dichloro-3-isothiazolidinone 1,1-dioxide
2-cyclopentyl-4,5-dichloro-3-isothiazolidinone 1,1-dioxide
2-phenyl-4,5-dichloro-3-isothiazolidinone 1,1-dioxide
2-(3,4-dibromophenyl)-4,5-dichloro-3-isothiazolidinone 1,1-dioxide
2-(4-chlorobenzyl)-4,5-dichloro-3-isothiazolidinone 1,1-dioxide
2-(2-hydroxypropyl)-4,5-dichloro-3-isothiazolidinone 1,1-dioxide
2-(3-chlorobutyl)-4,5-dichloro-3-isothiazolidinone 1,1-dioxide
2-(2-cyanoethyl)-4,5-dichloro-3-isothiazolidinone 1,1-dioxide
2-(2-carboxyethyl)-4,5-dichloro-3-isothiazolidinone 1,1-dioxide
2-carbethoxymethyl-4,5-dichloro-3-isothiazolidinone 1,1-dioxide
2-n-heptyl-4,5-diethyl-4,5-dichloro-3-isothiazolidinone 1,1-dioxide
4,4,5,5-tetrachloro-3-isothiazolidinone 1-oxide
2-methyl-4,4,5,5-tetrachloro-3-isothiazolidine 1-oxide
2-propyl-4,5-dimethyl-4,5-dichloro-3-isothiazolidinone 1-oxide
2-n-octadecyl-4,4,5,5-tetrachloro-3-isothiazolidinone 1-oxide
2,5-dimethyl-4,4,5-trichloro-3-isothiazolidinone 1-oxide
2-(4-chlorophenyl)-4,4,5,5-tetrachloro-3-isothiazolidinone 1-oxide
2-benzyl-5-methyl-4,4,5-trichloro-3-isothiazolidinone 1-oxide
2-(4-nitrobenzyl)-4,4,5,5-tetrachloro-3-isothiazolidinone 1-oxide
2-(4-methoxyphenyl)-4-methyl-4,5,5-trichloro-3-isothiazolidinone 1-oxide
2-(2-chloroethyl)-4,4,5,5-tetrachloro-3-isothiazolidinone 1-oxide
2-(2-carboxyethyl)-5-bromo-4,4,5-trichloro-3-isothiazolidinone 1-oxide
2-(2-carbethoxyethyl)-5-methyl-4,4,5-trichloro-3-isothiazolidinone 1-oxide
2-n-hexyl-4,4,5,5-tetrachloro-3-isothiazolidinone 1-oxide
2-n-octyl-4-ethyl-4,5,5-trichloro-3-isothiazolidinone 1-oxide
2-phenyl-4,4,5,5-tetrachloro-3-isothiazolidinone 1-oxide 2-(3-chlorophenyl)-4,4,5,5-tetrachloro-3-isothiazolidinone 1-oxide
2-(2-carbethoxyethyl)-4,4,5,5-tetrachloro-3-isothiazolidinone 1-oxide
5-methyl-4,4,5-trichloro-3-isothiazolidinone-1-oxide
4-bromo-4,5,5-trichloro-3-isothiazolidinone 1-oxide
4,4,5,5-tetrachloro-3-isothiazolidinone 1,1-dioxide
2,4-dimethyl-4,5,5-trichloro-3-isothiazolinone 1,1-dioxide
2-ethyl-4,4,5,5-tetrachloro-3-isothiazolidinone 1,1-dioxide
2-dodecyl-4,4,5,5-tetrachloro-3-isothiazolidinone 1,1-dioxide
2,5-dimethyl-4,4,5-trichloro-3-isothiazolidinone 1,1-dioxide
2-phenyl-4,4,5,5-tetrachloro-3-isothiazolidinone 1,1-dioxide
2-(4-chlorophenyl)-4,4,5,5-tetrachloro-3-isothiazolidinone 1,1-dioxide
2-benzyl-5-methyl-4,4,5-trichloro-3-isothiazolidinone 1,1-dioxide
2-(4-ethoxyphenyl)-4-ethyl-4,5,5-trichloro-3-isothiazolidinone 1,1-dioxide
5-ethyl-2-methyl-4,4,5-trichloro-3-isothiazolidinone 1,1-dioxide
2-(2-bromoethyl)-4,4,5,5-tetrachloro-3-isothiazolidinone 1,1-dioxide
2-methoxymethyl-4,4,5,5-tetrachloro-3-isothiazolidinone 1,1-dioxide
2-n-butyl-4,4,5,5-tetrachloro-3-isothiazone 1,1-dioxide
2-n-decyl-4,4,5,5-tetrachloro-3-isothiazolidinone 1,1-dioxide
4-methyl-2-phenyl-4,5,5-trichloro-3-isothiazolidinone 1,1-dioxide
2-benzyl-4-propyl-4,5,5-trichloro-3-isothiazolidinone 1,1-dioxide
2-chloromethyl-4,4,5,5-tetrachloro-3-isothiazolidinone 1,1-dioxide and the like The 3-isothiazolidinone 1-oxides and 1,1-dioxides of this invention can be prepared by a variety of synthetic routes. One method involves the oxidation of corresponding unoxidized 3-isothiazolidinones of the formula:

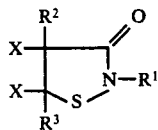

wherein $R^1$, $R^2$, $R^3$ and X are as defined in Formula I above. The 3-isothiazolidinones of Formula II can be prepared by the procedures described in U.S. Patent Application Ser. No. 336,650 filed on Feb. 28, 1973 by Ernest D. Weiler, assigned to a common assignee and which is herein incorporated by reference. These compounds are generally prepared by the halogenation of substituted 4-isothiazolin-3-ones of the formula

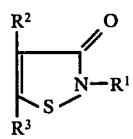

wherein $R^1$, $R^2$ and $R^3$ are as defined above. Halogenation of the substituted 4-isothiazolin-3-ones is generally carried out in a nonhydroxylic solvent such as ethyl acetate, butyl acetate, dimethylformamide, acetone, and the like. A variety of halogenating agents can be employed, for example, bromine, chlorine, sulfuryl chloride, sulfuryl bromide, and the like. An excess of halogenating agent can be employed if desired. The reaction is carried out over a broad temperature range of from about $-15°$ to about $120°$ C.

The substituted 4-isothiazolin-3-ones starting materials (Formula III) can be prepared by methods described in U.S. Pat. Nos. 3,523,121 and 3,761,488 of Lewis et al. granted Aug. 4, 1970 and Sept. 25, 1973, respectively, and U.S. Ser. No. 855,046, filed Sept. 3, 1969 by Lewis et al. and now abandoned, all of which are herein incorporated by reference. The 4-isothiazolin-3-ones in which $R^2$ is a methyl group can also be prepared by the cyclization of a dithiodiisobutyramide of the formula

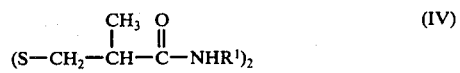

wherein $R^1$ is as defined above. The cyclization is generally carried out by the simultaneous addition of a halogenating agent and an amide, to a solvent, such as ethyl acetate, dimethylformamide, acetone or the like. The cyclization reaction is preferably carried out at a temperature from about $25°$ to about $70°$ C.

Depending on the reaction conditions employed for oxidation of compounds of Formula II, either the 1-oxide or 1,1-dioxide derivative or a mixture of these is produced. The 1-oxide derivative can be directly oxidized to the 1,1-dioxide derivatives. Oxidation can be accomplished by employing various types of oxidizing agents including peracids such as hydrogen peroxide, performic acid, peracetic acid, perphthalic acid, perbenzoic acid and m-chloroperbenzoic acid; oxides of nitrogen such as dinitrogen tetroxide; nitric acid; and chromic compounds such as chromium trioxide and chromic acid-sulfuric acid (Jones' reagent).

When peracids are employed for the oxidation and the 1-oxide derivative is desired, it is preferred to use no more than one equivalent of the peracid. To prepare the 1,1-dioxide derivative at least two equivalents are theoretically required, but three or more equivalents can be used. Although the oxidations can be run in the absence of a solvent, the use of a solvent is preferred. Any solvent which is not itself oxidized can be used and solvents in the ester ketone, aliphatic and aromatic hydrocarbon and chlorinated hydrocarbon classes are commonly employed. The chlorinated aliphatic hydrocarbons are preferred. The reactions can be run at temperatures from about $-5°$ C. to about $60°$ C. with the lower temperatures, e.g., from about $15°$ C., being preferred for the 1-oxide derivatives and the higher temperatures, e.g., from about $5°$ to about $50°$ C., being preferred for the 1,1-dioxide derivatives.

When an oxide of nitrogen such as $N_2O_4$ is employed, at least one equivalent is theoretically required for conversion to the 1-oxide derivative. With this type of oxidizing agent, oxidation to the 1,1-dioxide stage is more difficult and even with excesses of the dinitrogen tetroxide, the major product is the 1-oxide derivative. An inert solvent, for example, from the ester and chlorinated classes of solvents, is commonly employed although the reaction will proceed in the absence of a solvent. The reaction is usually run in the temperature range from about −5° to about 35° C. with from about 0° to about 15° C. being preferred. In some instances, the nitric acid salt of the 3-isothiazolidinone forms and this upon mild heating can be converted to the 1-oxide derivative.

When nitric acid is used as the oxidizing agent, the acid can have a concentration in the range from about 35 to about 70% with 65 to 70% being preferred. The reaction temperature can be from about −5° to about 35° C. with from about 0° to about 15° C. being preferred. The usual product is the 1-oxide derivative, which can be formed from the nitrate salt by mild heating in an aromatic hydrocarbon solvent e.g., in benzene.

When chromic acid is used as the oxidizing agent, it can be employed in from about 0.5 to about 2 or more equivalents. An inert solvent, such as ketonic solvent, is commonly employed although the oxidation will proceed in the absence of a solvent. The reaction is usually run at about room temperature, but will proceed at temperatures from about 0° to about 60° C. with from about 15° to about 35° C. being preferred.

The 3-isothiazolidinone 1-oxides of this invention can also be prepared by the concurrent halogenation and oxidation of compounds as defined in Formula III. Substantially equimolar or excess amounts of halogenating agents are employed depending upon whether the di, tri- or tetrahalo derivative is desired and depending upon the identity of R² and R³. The reaction is carried out in the presence of a non-oxidizable solvent, such as ethyl acetate, butyl acetate, acetone, chloroform and the like. The reaction is usually run in the temperature range from about −15° to about 120° C. with about −5° to 50° C. being preferred.

The chlorination of compounds having the formula

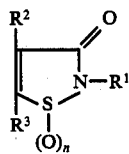

wherein R¹, R² and R³ and n are as defined in Formula I above can also be utilized to provide the 3-isothiazolidinone oxides of this invention. Any suitable chlorinating agent, such as chlorine or sulfuryl chloride, can be employed in equimolar or excess amounts depending upon whether the di-, tri or tetrahalo derivative is desired and depending upon the identity of R² and R³. Generally, an inert organic solvent is employed, such as ethylene dichloride, chloroform, ethyl acetate, butyl acetate, acetone, and the like. The chlorinated aliphatic hydrocarbons are preferred. The reaction is normally run in the temperature range of from about −15° to about 120° C. with temperatures between about −5° and 35° C. being preferred. Isolation of the products can be accomplished by any suitable means such as filtration of the insoluble reaction product or by concentration of the reaction mixture and subsequent purification of the product.

The 3-isothiazolidinone oxides of this invention can be prepared by the bromination of compounds having the formula

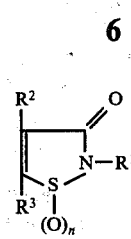

wherein R¹, R², R³ and n are as defined above to produce the corresponding 4,5 dibromo compound.

Reaction conditions such as temperature and choice of solvents are the same as those described for the chlorination reaction above. Any suitable brominating agent can be employed such as bromine or sulfuryl bromide. Equimolar ratios of reactants are preferred; however, an excess of brominating agent may be employed. The reaction is normally run in the temperature range of from about −15° to about 120° C. with temperatures between about −5° and 35° C. being preferred. Isolation of the product can be accomplished by any suitable means such as filtration of the insoluble reaction product or by concentration of the reaction mixture and subsequent purification.

The following illustrative examples are provided to enable one skilled in the art to better understand this invention, and are not to be considreed as limitations of the scope thereof.

ILLUSTRATIVE EXAMPLES

EXAMPLE 1 — Preparation of 4,5-dichloro-3-isothiazolidinone 1-oxide

To a solution of 2.2g. (0.02 mole) of 4-isothiazolin-3-one 1-oxide in 80 ml. ethylene dichloride (EDC) is added 2.4g. (0.02 mole) of sulfuryl chloride. The mixture is stirred at room temperature overnight. The white solid which forms is filtered, washed with EDC and air dried to yield 2.0g. (52%) of product.

EXAMPLE 2 — Preparation of 4,5-dichloro-2-n-octyl-3-isothiazolidinone 1-oxide

To a solution of 2.29g. (0.01 mole) of 2-n-octyl-4-isothiazolin-3-one 1-oxide in 3 ml. of EDC is added 1.2g. (0.01 mole) of sulfuryl chloride in 3 ml. of EDC. The mixture is stirred at room temperature over a weekend. The solution is filtered and concentrated to give an oil. The oil is further purified via column chromatography (100% benzene: silica) to give 1.0g. (33%) of product.

EXAMPLE 3 — Preparation of 4,5-dibromo-3-isothiazolidinone 1-oxide

To a solution of 2.2g. (0.02 mole) of 4-isothiazolin-3-one 1-oxide in 50 ml. of EDC is added 3.5g. (0.022 mole) of bromine in 10 ml. of EDC. The mixture is stirred overnight at room temperature. The white solid which separates is filtered, washed with EDC and dried to afford 3.2g. (54%) of product.

EXAMPLE 4 — Preparation of 4,5-dibromo-2-n-octyl-3-isothiazolidinone 1-oxide

Following the procedure of Example 3 the desired product is obtained in a 61% yield.

EXAMPLE 5 — Preparation of 4,5-dibromo-2-ethyl-3-isothiazolidinone 1-oxide

Following the procedure of Example 3 the desired product is obtained in a 34% yield.

EXAMPLE 6 — Preparation of 4,5-dibromo-2-n-butyl-3-isothiazolidinone 1-oxide Following the procedure of Example 3 the desired product is obtained.

EXAMPLE 7 — Preparation of 4,5-dichloro-2-methyl-3-isothiazolidinone 1-oxide To a suspension of 76g. (0.5 mole) of crude 2-methyl-4-isothiazolin-3-one hydrochloride in 500 ml. of ethyl acetate is added over 1 hr., 177g. (2.5 mole) of chlorine. The temperature reaches a high of 58° C. in 15 minutes and is raised to 65° C. by external heating, where it is held until the end of the chlorine addition. The solution is allowed to cool and filtered to remove traces of dark solid. The filtrate is evaporated under reduced pressure to a dark amber oil. On standing, the oil partially solidifies. Trituration of the mixture of oil and solid gives a cream colored solid which is collected by filtration. Crystallization of this material from ethanol gives 10.6g. (10.4%) of product as a white solid.

EXAMPLE 8 — Preparation of 2-methyl-4,4,5,5-tetrachloro-3-isothiazolidinone-1-oxide To a solution of 2.55g. (0.01 mole) of 2-methyl-4,4,5,5-tetrachloro-3-isothiazolidinone in 10 ml. of chloroform at 0° is added a solution of 2.03g. (0.01 mole) of m-chloroperbenzoic acid (85% Technical) in 60 ml. of chloroform. The mixture is allowed to warm to room temperature and stand over a weekend. The solution is cooled in dry ice. White solid (m-chlorobenzoic acid) separates (0.91g.) and is removed by filtration. The filtrate is washed in a separatory funnel with 50 ml. of water containing 0.4g. of sodium bicarbonate. The chloroform solution is separated and dried over magnesium sulfate. Evaporation gives 2.54g. of crude product as a white solid.

EXAMPLE 12 — Preparation of 2-n-butyl-4,4,5,5-tetrachloro-3-isothiazolidinone 1-oxide To a solution of 15.7g. (0.1 mole) of 2-n-butyl-4-isothiazolin-3-one in 100 ml. of ethyl acetate is added, over ½ hour, 21.3g. (0.3 mole) of chlorine. The temperature is allowed to rise to a high of about 62°, during which time solid first separates and then redissolves. The solution is concentrated under reduced pressure to give 26.5g. of a yellow oil. A TLC (silica/toluene) shows two major components. The oil is then chromatographed on a dry-column with toluene. Extraction of the leading half of the column with ether followed by evaporation gives the crude product. Distillation provides pure 2-n-butyl-4,4,5,5-tetrachloro-3-isothiazolidinone 1-oxide.

Following the procedure of Example 8, the desired product is obtained.

EXAMPLE 13 — Preparation of 2-octyl-4,5-dichloro-3-isothiazolidinone 1,1-dioxide To a solution of 2.84g. (0.01 mole) of 2-octyl-4,5-dichloro-3-isothiazolidinone 1-oxide in 20 ml. of chloroform at 0° C. is added a solution of 5.4g. (0.025 mole) of 81% pure m-chloroperbenzoic acid in 100 ml. of chloroform. The mixture is stirred for three days at 50° C. The reaction mixture is filtered and the filtrate is washed with a dilute sodium bicarbonate solution. The chloroform layer is dried over magnesium sulfate and evaporated to give the crude product.

EXAMPLE 14 — Preparation of 4,5-dichloro-5-methyl-3-isothiazolidinone-1-oxide Following the procedure in Example 2, the desired 4,5-dichloro-5-methyl-3-isothiazolidinone-1-oxide is obtained.

EXAMPLE 15 — Preparation of 4,5-dichloro-3-isothiazolidinone-1,1-dioxide

Following the procedure of Example 13, the desired 4,5-dichloro-3-isothiazolidinone-1,1-dioxide is obtained.

TABLE II $$\begin{array}{c} X \quad O \\ R^2 \diagdown \diagup \diagup \\ R^3 \diagdown \diagdown N{-}R^1 \\ X \diagup S \diagdown \\ (O)_n \end{array}$$

| Example No. | $R^1$ | $R^2$ | $R^3$ | X | n |
|---|---|---|---|---|---|
| 1 | H | H | H | 4,5-Cl | 1 |
| 2 | n-$C_8H_{17}$ | H | H | 4,5-Cl | 1 |
| 3 | H | H | H | 4,5-Br | 1 |
| 4 | n-$C_8H_{17}$ | H | H | 4,5-Br | 1 |
| 5 | $C_2H_5$ | H | H | 4,5-Br | 1 |
| 6 | n-$C_4H_9$ | H | H | 4,5-Br | 1 |
| 7 | $CH_3$ | H | H | 4,5-Cl | 1 |
| 8 | $CH_3$ | Cl | Cl | 4,5-Cl | 1 |
| 9 | $C_2H_5$ | H | H | 4,5-Br | 2 |
| 10 | —$CH_2$—⟨C₆H₃Cl₂⟩ | Cl | Cl | 4,5-Cl | 1 |
| 11 | —$CH_2$—⟨C₆H₄CN⟩ | Cl | Cl | 4,5-Cl | 1 |
| 12 | n-$C_4H_9$ | Cl | Cl | 4,5-Cl | 1 |
| 13 | n-$C_8H_{17}$ | H | H | 4,5-Cl | 2 |
| 14 | H | H | $CH_3$ | 4,5-Cl | 1 |
| 15 | H | H | H | 4,5-Cl | 2 |

The following Table I presents the elemental analysis and melting points of compounds prepared via the above experimental procedures.

Table I

| Example No. | mp° C. | Elemental Analysis | | | Found/Calc'd | |
|---|---|---|---|---|---|---|
| | | C | H | N | S | X |
| 1 | 172–4 | 19.46 (19.16) | 1.64 (1.61) | 7.30 (7.45) | 17.67 (17.05) | 37.85 (37.71) |
| 2 | 47–9 | 44.11 (44.00) | 6.56 (6.38) | 4.55 (4.66) | 10.81 (10.68) | 23.85 (23.62) |
| 3 | 149–51 | 13.20 (13.01) | 1.30 (1.09) | 4.93 (5.05) | 11.26 (11.58) | 57.44 (57.71) |
| 4 | oil | 35.74 (33.95) | 5.05 (4.92) | 3.29 (3.60) | 8.09 (8.24) | 41.44 (41.07) |
| 5 | 97–9 | 19.41 (19.67) | 2.49 (2.30) | 4.30 (4.59) | 10.56 (10.49) | 50.66 (52.46) |
| 6 | oil | 26.44 (25.24) | 3.67 (3.32) | 4.52 (4.20) | 8.74 (9.62) | 45.22 (47.98) |
| 7 | 136–8 | 23.79 (23.76) | 2.46 (2.48) | 6.81 (6.93) | 14.66 (15.84) | 35.28 (35.15) |
| 8 | 99–102 | 18.37 (17.71) | 1.03 (1.11) | 5.18 (5.17) | 11.82 (11.81) | 52.35 (52.40) |
| 9 | 58–61 | 19.69 (18.69) | 2.61 (2.18) | 4.91 (4.36) | 10.51 (9.97) | 48.40 (49.84) |
| 10 | 112–5 | 29.08 (28.87) | 1.27 (1.21) | 3.34 (3.35) | 7.64 (7.71) | |
| 11 | 142–4 | 35.39 (35.51) | 1.65 (1.61) | 7.30 (7.53) | 8.61 (8.62) | |

The novel halogenated 3-isothiazolidinone 1-oxides and 1,1-dioxides of this invention are biocidally active. Representative compounds demonstrate control of various weeds, phytopathogenic fungi and microorganisms such as bacteria, fungi and algae.

One method of evaluation for the control of microorganisms is a procedure known as a streak test. In this test the compounds to be examined are dissolved in an appropriate solvent and added to two sterile Petri plates in an amount necessary to provide 1000 ppm of the compound in one plate and 100 ppm in the other plate when diluted with 20 ml. of the appropriate nutrient agar. The compound and the agar are thoroughly mixed and allowed to harden. The agar surface is streaked with agar-grown cultures of bacteria: *Pseudomonas aeruginosa*, Staphylococcus, aureus and Escherichia coli; fungi: *Aspergillus niger* and Rhizopus spp. and algae; *Chlorella pyrenoidosa* and *Black algae*. The plates are then incubated at the appropriate time and temperature for the given culture and then observed for inhibition of growth.

Antibacterial activity was also evaluated by a Serial Dilution Test (Broth Titer Test) wherein a series of broths containing varying dilutions of a test compound and an organism are halved starting with 1:1000. The values obtained represent the maximum dilution at which the compound under evaluation renders complete control of the organism. The results of these tests are shown below in Table III.

Table III

| Example No. | Microbiocidal Control | | |
|---|---|---|---|
| | Algae | Fungi | Bacteria |
| 1 | 3[a] | 4[a] | 3[a] |
| 2 | 20 | 500 | 1000 |
| | 20 | 500 | 1000 |
| 3 | 2 | 500 | 125 |
| | | | 125 |
| | | | 31 |
| | | | 125 |
| 4 | 5 | 16 | 125 |
| | 2.5 | 31 | 4 |
| 5 | 4[a] | 4[a] | 4[a] |
| 6 | 5 | 63 | — |
| | 2.5 | 31 | 125 |
| | | | 63 |
| 7 | 500 | — | 500 |
| | 500 | | 500 |
| 8 | — | — | 500 |
| | | | 500 |
| | | | 500 |
| 9 | — | — | 500 |
| | | | 500 |
| | | | 500 |

[1] Preliminary agar streak test (average value shown)
[2] Serial dilution values given in ppm in the following order; algae: Chlorella and Black algae; Fungi: A. niger and Rhizopus; Bacteria: Pseudomonas, S. aureus and E. coli Representative compounds of this invention were also evaluated as fungicides in standard greenhouse tests. A foliar spray of the compounds containing 150 ppm gave protection against tomato late blight (*Phytophthora infestans*); rice blast (*Piricularia oryzae*); bean powdery mildew (*Erysiphe polygoni*) and blight (*Cercospora spp*). The results of these are shown below in Table IV.

Table IV

| Example No. | Fungicidal Control[a] | | | | |
|---|---|---|---|---|---|
| | Foliar Spray (150 ppm)[b] | | | | |
| | PM | RB | LB | CB | P |
| 1 | C | C | A | B | NT |
| 2 | NT | NT | NT | NT | NT |
| 3 | C | C | C | NT | B |
| 4 | C | C | A | A | A |
| 5 | C | NT | C | NT | NT |

Table IV-continued

| Example No. | Fungicidal Control[a] | | | | |
|---|---|---|---|---|---|
| | Foliar Spray (150 ppm)[b] | | | | |
| | PM | RB | LB | CB | P |
| 8 | B | NT | NT | NT | NT |

[a] A = 97-100%; B = 90-96%; C = 70-89%; D = 50-69% E = >50% Disease control at concentration of 150 ppm.
[b] PM = Powdery mildew
RB = Rice blast
LB = Late blight
CB = Cercospora blight
P = Pythium on beet
NT = Not tested Representative compounds of this invention were evaluated in a standard postemergence type herbicide test. In this test, two-week old plants are sprayed with the test compound at a rate of 10 lbs. per acre. Four monocotyledonous species namely millet (*Setaria italica*), rye grass (*Lolium miltiflorum*), sorghym (*Sorghym vulgare*) and wildoats (*Avena fatua*) and four dicotyledonous plants curly dock (*Rumex crispus*), flax (*Linum usitatissimum*) tomatoes (*Lycopersicum esculentum*) and velvetleaf (*Abutilon theophrasti*) were used. The percent injury is measured two weeks after application. The results of these test are given below in Table V.

Table V

| Example No. | Herbicidal Control | |
|---|---|---|
| | % Herbicidal Postemergence Control[a] | |
| | Monocots | Dicots |
| 1 | 50 | 77 |
| 2 | NT | NT |
| 3 | 72 | 90 |
| 4 | 37 | 40 |
| 5 | 92 | 92 |

[a] Preliminary herbicidal data at spray application rate of 10 lbs. per acre.

When used as plant bactericides or fungicides, the isothiazolidinone 1-oxides and 1,1-dioxides of this invention are generally applied at a rate of about 0.1 to 25 pounds per acre, and preferably about 0.25 to about 10 pounds per acre. The rate of application is usually dependent on the isothiazolidinone 1-oxide or 1,1-dioxide used, the phytopathogenic organism to be controlled the method and type of application, and other similar factors.

Generally, control of a living or anism is achieved in accordance with this invention by contacting the organism with an isothiazolidinone 1-oxide or 1,1-dioxide in an amount which is effective to control the organism. Any of the techniques known in the art can be employed to disseminate the isothiazolidinone oxides in a manner so as to achieve the desired contact with the organism to be controlled.

The compounds of this invention can be readily utilized as slimicides, algaecides, bactericides, and fungicides in any locus and particularly in aqueous media, such as, for example, water-cooling systems, swimming pools, paper pulp processes, aqueous polymer dispersions, water-based paints, and the like. In addition, these compounds and compositions containing them can function as, for example, fabric and leather preservatives, cosmetic preservatives, soap additives, sanitizing agents, such as in laundry soaps and detergents, preservatives for metal working compounds, such as emulsifiable cutting oils, preservatives for fuels, fiber spin finish biocides, and the like.

The isothiazolidinones 1-oxides and 1,1-dioxides of the invention are also useful as laundry sanitizing agents, in which fast speed-of-kill is particularly advantageous. Generally, about 0.01 to about 10% by weight and preferably about 0.05 to about 5% by weight, of the isothiazolidinone oxide will be added to a soap detergent to make a sanitizing laundry composition. Isothiazolidinone oxides can also be added directly to the laundry wash water, generally at a concentration of about 0.5 to about 1000 parts per millions by weight.

In general, a locus subject to contamination by microorganisms can be protected in accordance with this invention by incorporating into the locus an isothiazolidinone 1-oxide 1,1-dioxides in an amount which is effective to control the microorganisms. The term "contamination" is meant to include attack by microorganisms which leads to a chemical or physical breakdown or disintegration of the locus as well as proliferation of the microorganisms within the locus without an accompanying deleterious effect. The exact amount of isothiazolidinone 1-oxide or 1,1-dioxide required will, of course, vary with the medium being protected, the microorganisms being controlled, the particular isothiazolidinones oxides or compositions containing the isothiazolidinones oxides being employed, the degree of control desired, and other factors. Typically, in a liquid medium suitable control is obtained when the isothiazolidinones oxides are incorporated in the range of from about 0.1 to about 10,000 parts per million (ppm) or from about 0.00001 to about 1% based on the weight of the medium. A range of about 1 to 2000 ppm is preferred.

The term "control" is employed in the specification and claims of this application is to be construed as the effect of any means which adversely affects the existence or growth of any living organism or microorganism. This effect may comprise complete killing action, eradication, arresting in growth, inhibition, reduction in number or any combination of these effects.

The isothiazolidinone 1-oxides and 1,1-dioxides of the invention are also useful as paint preservatives and paint fungistats. Microbial activity in water-based and oil-based paint emulsions is inhibited when the isothiazolidinones oxides are incorporated into the paint. The isothiazolidinones oxides are also mildewcide for paint films when incorporated in paint formulations.

The isothiazolidinone 1-oxide and 1,1-dioxides of this invention are especially useful as agricultural bactericides and fungicdes. As such as they are particularly valuable when formulated in bactericidal and fungicidal compositions. Such compositions normally comprise an agronomically acceptable carrier and an isothiazolidinone 1-oxide or 1,1-dioxide or mixture of isothiazolidinone oxides as the active agent. Where necessary or desirable, surfactants or other additives may be incorporated to give uniformly formulated mixtures. By "agronomically acceptable carrier" is meant any substance which can be utilized to dissolve, dispense, or diffuse the chemical incorporated therein without impairing the effectiveness of the toxic agent and which does no permanent damage to the environment, soil, equipment, or agronomic crops.

For use as pesticides, the compounds of this invention are usually taken up in an agronomically acceptable carrier or formulated so as to render them suitable for subsequent dissemination. For example, the isothiazolidinone 1-oxides and 1,1-dioxides can be formulated as wettable powders, emulsion concentrates, dusts, granular formulations, aerosols or flowable emulsifiable concentrates. In such formulations, the isothiazolidinone oxides are extended with a liquid or solid carrier and, when desired, suitable surfactants are incorporated.

Compounds of this invention can be dissolved in a water-miscible liquid, such as ethanol, isopropanol, acetone, and the like. Such solutions are easily extended with water.

The isothiazolidinone 1-oxides and 1,1-dioxide can be taken up on or mixed with a finely particled solid carrier, as for example, clays, inorganic silicates, carbonates, and silicas. Organic carriers can also be employed. Dust concentrates are commonly made wherein isothiazolidone oxides are present in the range of from about 20 to about 80%. For ultimate applications these concentrates are normally extended with additional solid from about 1 to about 20%.

Wettable powder formulations are made by incorporating the compounds of this invention in an inert, finely divided solid carrier along with a surfactant which may be one or more emulsifying, wetting, dispersing or spreading agents or blends of these. The isothiazolidinone oxides are usually present in the range of from about 10 to about 80% by weight and the surfactants in from about 0.5 to about 10% by weight. Commonly used emulsifying and wetting agents include polyoxyethylated derivatives of alkylphenols, fatty alcohols, fatty acids and alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehyde-naphthalene sulfonates.

One convenient method for preparing a solid formulation is to impregnate the isothiazolidinone 1-oxide or 1,1-dioxide toxicant onto the solid carrier by means of a volatile solvent, such as acetone. In this manner adjuvants, such as activators, adhesives, plant nutrients, synergists and various surfactants, can also be incorporated.

Emulsifiable concentrate formulations can be prepared by dissolving the isothiazolidinone 1-oxide and 1,1-dioxide of this invention in an agromonically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents may constitute from about 0.5 to about 10% by weight of the emulsifiable concentrate and may be anionic, cationic or non-ionic in character. Anionic surfactants include alcohol sulfates or sulfonates, alkylarene sulfonates and sulfosuccinates. Cationic surfactants include fatty acid alkylamine salts and fatty acid alkyl quaternaries. Non-ionic emulsifying agents include alkylene oxide adducts of alkylphenols, fatty alcohols, mercaptans and fatty acids. The concentration of the active ingredients may vary from about 10 to about 80%, preferably in the range of about 25 to about 50%.

For use as phytopathogenic agents, these compounds should be applied in an effective amount sufficient to exert the desired biocidal activity by techniques well known in the art. Usually, this will involve the application of the isothiazolidinone oxides to the locus to be protected in an effective amount when incorporated in an agronomically acceptable carrier. However, in certain situations, it may be desirable and advantageous to apply the compounds directly onto the locus to be protected without the benefit of any substantial amount of carrier. This is a particularly effective method when the physical nature of the isothiazolidinone 1-oxide is such as to permit what is known as "low volume" application, that is, when the compounds are in liquid form or substantially soluble in higher boiling solvents.

The application rate will, of course, vary depending upon the purpose for such application, the isothiazolidinone 1-oxides and 1,1-dioxides being utilized, the frequency of dissemination and the like.

For use as agricultural bactericides and fungicides, dilute sprays can be applied at concentrations of from about 0.05 to about 20 pounds of the active isothiazolidinone 1-oxide or 1,1-dioxide ingredient per 100 gallons of spray. They are usually applied at from about 0.1 to about 10 pounds per 100 gallons and preferably at about 0.125 to about 5 pounds per 100 gallons. In more concentrated sprays, the active ingredient is increased by a factor of about 2 to 12. With dilute sprays, applications are usually made to the plants until run-off is achieved; whereas, with more concentrated or low-volume sprays, the materials are applied as mists.

The compounds of this invention may be utilized as the sole biocidal agents or they may be employed in conjunction with other fungicides, bactericides, algaecides, slimicides, insecticides, miticides, or with other comparable pesticides.

It is to be understood that changes and variations may be made without departing from the spirit and scope of the invention as defined by the appended claims.

We claim:

1. A compound of the formula

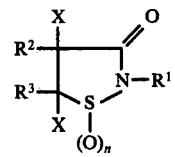

wherein $R^1$ is hydrogen; $(C_1-C_{18})$ unsubstituted alkyl or hydroxy, halogen, $(C_1-C_4)$ carbalkoxy, cyano or carboxy monosubstituted $(C_1-C_{18})$ alkyl; a cycloalkyl group having a $(C_3-C_8)$ cycloalkyl ring and up to 12 carbon atoms; unsubstituted benzyl, or halogen-, $(C_1-C_4)$ alkyl-, $(C_1-C_4)$ alkoxy-, nitro or cyano-substituted benzyl; phenyl or naphthyl, or halogen-, $(C_1-C_4)$ alkyl, or nitro- substituted phenyl or naphthyl;

X is halogen; and $n$ is 1 or 2.

2. A compound according to claim 1 wherein $n$ is 1.

3. A compound according to claim 2 wherein $R^1$ is hydrogen; unsubstituted $(C_1-C_{18})$ alkyl; $(C_3-C_8)$ cycloalkyl; unsubstituted benzyl, or halogen-, $(C_1-C_4)$ alkyl- or $(C_1-C_4)$ alkoxy-substituted benzyl; phenyl, or halogen-, methyl- or nitro-substituted phenyl; $(C_1-C_4)$ hydroxyalkyl; $(C_1-C_4)$ haloalkyl; $(C_1-C_4)$ carbalkoxyalkyl; $(C_1-C_4)$ cyanoalkyl or $(C_1-C_4)$ carboxyalkyl; and X is halogen.

4. A compound according to claim 3 wherein X is chlorine, $R^1$ is unsubstituted $(C_1-C_8)$ alkyl, and $R^2$ and $R^3$ are hydrogen or halogen.

5. A compound according to claim 3 wherein X is bromine, and $R^2$ and $R^3$ are hydrogen or halogen.

6. A compound according to claim 4 wherein $R^1$ is n-octyl, and $R^2$ and $R^3$ are hydrogen.

7. A compound according to claim 5 wherein $R^1$ is n-octyl, and $R^2$ and $R^3$ are hydrogen.

8. A compound according to claim 4 wherein $R^1$ is hydrogen, and $R^2$ and $R^3$ are hydrogen.

9. A compound according to claim 5 wherein $R^1$ hydrogen, and $R^2$ and $R^3$ are hydrogen.

* * * * *

UNITED STATES PATENT AND TRADEMARK OFFICE
CERTIFICATE OF CORRECTION

PATENT NO. : 4,062,859
DATED : December 13, 1977
INVENTOR(S) : Ernest D. Weiler and George A. Miller It is certified that error appears in the above-identified patent and that said Letters Patent are hereby corrected as shown below:

Claim 1, Column 14, line 18, after "naphthyl;" insert -- $R^2$ and $R^3$ are independently a hydrogen atom, a halogen atom or an alkyl group of from 1 to 4 carbon atoms; --

Signed and Sealed this

Twenty-second Day of August 1978

[SEAL]

Attest:

RUTH C. MASON
Attesting Officer

DONALD W. BANNER
Commissioner of Patents and Trademarks